(12) United States Patent
Khan et al.

(10) Patent No.: US 8,802,441 B2
(45) Date of Patent: Aug. 12, 2014

(54) METHOD OF SYNTHESIZING COLLOIDAL NANOPARTICLES

(75) Inventors: Saif A. Khan, Singapore (SG); Suhanya Duraiswamy, Singapore (SG)

(73) Assignee: National University of Singapore, Singapore (SG)

( * ) Notice: Subject to any disclaimer, the term of this patent is extended or adjusted under 35 U.S.C. 154(b) by 82 days.

(21) Appl. No.: 13/040,860

(22) Filed: Mar. 4, 2011

(65) Prior Publication Data

US 2011/0215277 A1 Sep. 8, 2011

Related U.S. Application Data

(60) Provisional application No. 61/310,394, filed on Mar. 4, 2010.

(51) Int. Cl.
*G01N 35/08* (2006.01)

(52) U.S. Cl.
USPC .............................................. 436/53; 436/52

(58) Field of Classification Search
CPC .................. B01J 2219/00466; Y10S 514/937
USPC .............................................. 436/53; 516/21
See application file for complete search history.

(56) References Cited

U.S. PATENT DOCUMENTS

2007/0003442 A1* 1/2007 Link et al. ....................... 422/99

* cited by examiner

*Primary Examiner* — Natalia Levkovich
(74) *Attorney, Agent, or Firm* — Osha Liang LLP

(57) ABSTRACT

There is provided a method for synthesizing colloidal nanoparticles comprising the step of creating a reactive three-phase foam containing reactants therein for synthesizing the colloidal nanoparticles.

17 Claims, 7 Drawing Sheets

METHOD OF SYNTHESIZING COLLOIDAL NANOPARTICLES

CROSS-REFERENCE TO RELATED APPLICATIONS

This application claims benefit to U.S. Provisional Application 61/310,394 filed on Mar. 4, 2011, the disclosure of which is hereby incorporated by reference.

BACKGROUND OF INVENTION

1. Technical Field

The present invention generally relates to a method of synthesizing colloidal nanoparticles. The present invention also relates to a system for synthesizing the same.

2. Background

Continuous flow-based micro-fluidic synthesis methods operate at steady state and offer superior control over reaction conditions such as reagent addition, mixing and temperature. Scale-up to higher throughputs is straightforward in principle, and involves parallel operation of multiple reactor units. Several research groups have leveraged on one or more of these advantages and successfully demonstrated the wet chemical synthesis of semiconducting, metallic, dielectric, magnetic and core-shell nano-particles. However, the high surface-to-volume ratios in continuous micro-fluidic reactors imply significant particle deposition and aggregation on micro-channel walls, which leads to rapid, irreversible particle deposition and thus degradation of product quality with time. Hence isolation of growing particles from the micro-channel walls becomes a requirement in these techniques.

Another method to form colloids is to use bulk-solution-phase methods. However, as reagent homogenization and chemical reaction proceed simultaneously in the reaction vessel, it becomes very difficult to control the final outcome. Hence, the synthesis of colloidal nanomaterials via bulk solution-phase methods remains a difficult and somewhat of an "art" even after the discovery of suitable chemical ingredients and all else remaining the same, there is much that is dependent on the "synthetic skills" of the chemist. Hence, this method is unreliable and does not produce consistent results.

As an alternative to bulk solution-phase synthesis, confinement of reagents in dispersed water drops of a water-in-oil micro-emulsion has been extensively studied. Such systems, where self-assembled surfactant micelles function as individual batch reactors have been used for the synthesis of a broad range of colloidal nano-materials. However, the scalability of this method is limited by the emulsification procedure employed and it is commonly not possible to control reagent dispensing at the scale of a single micelle.

An alternative approach involves the use of droplet microfluidics to overcome the above-mentioned drawbacks. The main drawback limiting the general applicability of such methods is the sensitive dependence of flow pattern on fluid properties such as interfacial tension. Fluid properties are usually dictated by the reagents required for synthesis, and are usually act independent design variables. Hence, it remains a challenge to decouple the dependence of flow patterns from the fluid properties. Further, such a method can result in fouling of the micro-fluidic device since the size of the droplets cannot be controlled adequately.

There is a need to provide a micro-fluidic device that overcomes, or at least ameliorates, one or more of the disadvantages described above.

There is a need to provide a method for colloidal synthesis that that overcomes, or at least ameliorates, one or more of the disadvantages described above.

SUMMARY OF INVENTION

According to a first aspect of the invention, there is provided a method for synthesizing colloidal nanoparticles comprising the step of creating a reactive three-phase foam containing reactants therein for synthesizing the colloidal nanoparticles.

Advantageously, the method provides precise control of at least one phase, preferably two phases and more preferably three phases of the three-phases for synthesizing colloidal nanoparticles, such that the synthesized colloidal nanoparticles can be produced having a narrow particle size distribution.

Advantageously, the three-phases may be used to more precisely control the conditions for synthesis of the nanoparticles. Advantageously, in one embodiment, one of the phases of said foam is a continuous phase which acts as a carrier for carrying "reactive" aqueous phase cells in which reactants are located for reacting and producing the nanoparticles while another gas phase cells acts as a "separator" to keep the adjacent reactive aqueous phase cells separated. More advantageously, the three-phases may be produced in an ordered manner in that there is provided aqueous phase cells separated by intervening gas cells that are both contained within a continuous oil phase.

Yet more advantageously, the three-phase foam may be produced in a microfluidic device and because once the cells containing the reactant phases are formed, they do not interact with each other as well as with the walls of the microfluidic device, and therefore do not foul any channels of the microfluidic device. This is very important particularly when manufacturing nanoparticles using a microfluidic device which are very prone to such fouling and are often rendered inoperable once fouling has occurred.

In one embodiment, the method comprises the step of providing seed nano-particles dispersed in the aqueous phase. In one embodiment, the seed nano-particles are silica nanoparticles coated with gold nano-particles thereon. The gold nano-particles may be about 3 nm to about 5 nm in diameter. In another embodiment, the seed nano-particles are gold nano-particles.

In one embodiment, the method comprises the step of forming an ordered three-phase fluid flow comprising alternating aqueous phase and gas phase immersed in a continuous oil phase. Advantageously, each alternating compartment may be viewed as an individual batch reactor, such that the colloidal synthesis of nanoparticles may be controlled with increased precision.

According to a second aspect of the invention, there is provided a three-phase reactive foam containing reactants therein for synthesizing colloidal nano-particles.

According to a third aspect of the invention, there is provided a microreactor system for synthesizing colloidal nano-particles comprising: at least two inlet conduits containing fluids therein, at least two of said fluids being immiscible with each other; mixing means in fluid communication with and positioned downstream of said at least two inlet conduits and being configured to mix said immiscible fluids to form a two-phase fluid flow; a continuous phase conduit in fluid communication with and positioned downstream of said mixing means for coating said two-phase fluid flow and thereby producing a three-phase fluid flow; and an outlet conduit positioned downstream of said continuous phase conduit for releasing said three-phase fluid flow, wherein said three-phase fluid contains reactants for synthesizing the colloidal nanoparticles.

In one embodiment, the at least two inlet conduits may be configured to converge and join the continuous phase conduit at a junction. In one embodiment, the inlet conduits are in fluid communication with the mixing means in the form of a microchamber which is upstream of, and in fluid communication with, the continuous phase conduit. In one embodiment, the microchamber has an outlet which is substantially perpendicular to the radial axis of the continuous phase conduit. In this embodiment, the microchamber forms a substantially "T-shaped" junction with the continuous phase conduit.

In a further embodiment, the inlet conduits join the microchamber at about 30 degrees to about 150 degrees relative to a horizontal plane that extends through the microchamber. In this embodiment, an inlet conduit joins the microchamber at a range of angles selected from the group consisting of about 30 degrees to about 150 degrees, about 40 degrees to about 150 degrees, about 50 degrees to about 150 degrees, about 60 degrees to about 150 degrees, about 70 degrees to about 150 degrees, about 80 degrees to about 150 degrees, about 90 degrees to about 150 degrees, about 100 degrees to about 150 degrees, about 110 degrees to about 150 degrees, about 120 degrees to about 150 degrees, about 130 degrees to about 150 degrees, about 140 degrees to about 150 degrees, about 30 degrees to about 140 degrees, about 30 degrees to about 130 degrees, about 30 degrees to about 120 degrees, about 30 degrees to about 110 degrees, about 30 degrees to about 100 degrees, about 30 degrees to about 90 degrees, about 30 degrees to about 80 degrees, about 30 degrees to about 70 degrees, about 30 degrees to about 60 degrees, about 30 degrees to about 50 degrees, and about 30 degrees to about 40 degrees. Advantageously, the above mentioned angles enable strictly alternate dispensing of gas and liquid cells in the third oil phase.

The continuous phase conduit may have a range of diameters selected from the group consisting of about 50 μm to about 1000 μm, about 100 μm to about 1000 μm, about 300 μm to about 1000 μm, about 500 μm to about 1000 μm, about 700 μm to about 1000 μm, about 50 μm to about 700 μm, about 50 μm to about 500 μm, about 50 μm to about 300 μm, and about 50 μm to about 100 μm. Where the cross-sectional area of the continuous phase conduit is substantially non-spherical, the diameter may refer to the equivalent diameter of the continuous phase conduit, wherein said equivalent diameter is relative to a completely spherical diameter. In some embodiments, the cross-section of the continuous phase conduit is completely spherical and the equivalent diameter is equal to the actual diameter of the continuous phase conduit. Advantageously, the above mentioned dimensions also promote laminar flow in the microchamber as the two fluids mix.

Advantageously, due to the dimensions of the continuous phase conduit and the inlet conduits, the immiscible fluids in the dispersed phase may be maintained in the laminar region.

According to a fourth aspect of the invention, there is provided a microreactor comprising: at least two inlet conduits for containing fluids therein in which at least two of said fluids are immiscible with each other; mixing means in fluid communication with and positioned downstream of said at least two inlet conduits and being configured to mix said immiscible fluids to form a two-phase fluid flow; a continuous phase conduit in fluid communication with and positioned downstream of said mixing means for coating said two-phase fluid flow and thereby producing a three-phase fluid flow; and an outlet conduit positioned downstream of said continuous phase conduit for releasing said three-phase fluid flow

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

The inset shows a TEM image of a representative particle population. Scale bar represents 200 nm.

Figure 9:
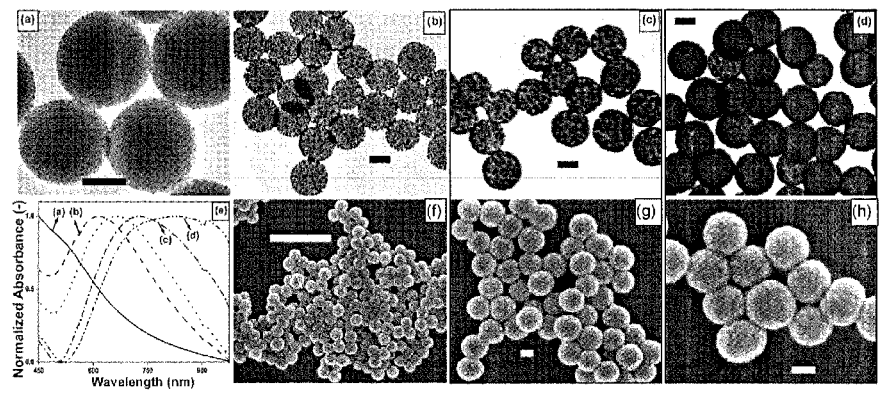

FIG. 9a is a TEM image of a gold-seeded silica particle solution showing 3 nm gold seeds (dark spots) on silica particles. The average spacing between adjacent seeds is about 7 nm. The scale bar represents 100 nm.

FIG. 9b is a TEM image of a gold-seeded silica particle solution showing 10 nm gold seeds (dark spots) on silica particles. The scale bar represents 100 nm.

FIG. 9c is a TEM image of a gold-seeded silica particle solution showing 35 nm gold seeds (dark spots) on silica particles. The scale bar represents 100 nm.

FIG. 9d is an image showing further growth and coalescence of the flattened nanoislands. The scale bar represents 100 nm.

FIG. 9e is the corresponding UV-visible absorbance spectra of the particle solutions from FIG. 9a to FIG. 9d.

FIG. 9f is the SEM image corresponding to the particle solution from FIG. 9b. The scale bar represents 1000 nm.

FIG. 9g is the SEM image corresponding to the particle solution from FIG. 9c. The scale bar represents 100 nm.

FIG. 9h is the SEM image corresponding to the particle solution from FIG. 9d. The scale bar represents 100 nm.

Figure 10:

FIG. 10a is a photograph of gold-seeded silica particle solution. FIG. 10b is a photograph of a solution of silica particles decorated with 10 nm gold nanoislands. FIG. 10c is a photograph of a solution of silica particles decorated with 35 nm gold nanoislands. FIG. 10d is a photograph of a solution of silica particles with nearly coalesced gold nanoislands. FIG. 10e is a photograph of a solution of silica particles with completely smooth gold shell of thickness 30 nm.

Figure 11:
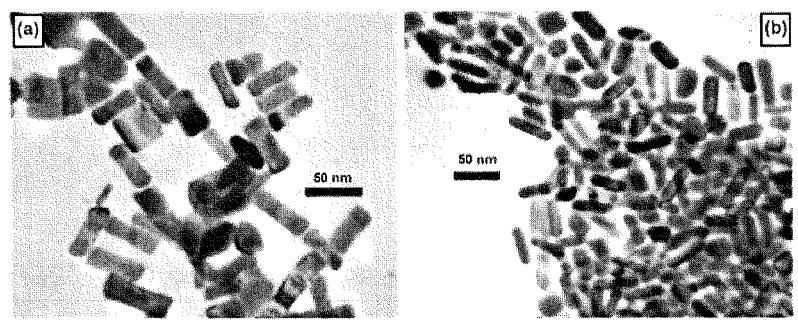

FIG. 11a and FIG. 11b are TEM images of gold nanorods made according to a disclosed embodiment. The aspect ratio of the gold nanorods in FIG. 11a is about 5 while the aspect ratio of the gold nanorods in FIG. 11b is about 4.

Figure 12:
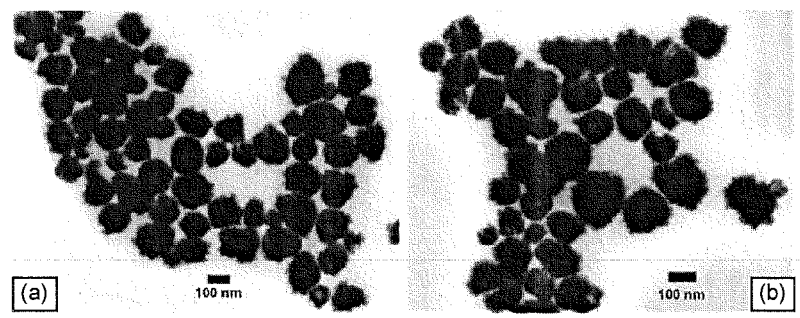

FIG. 12a and FIG. 12b are TEM images of silver nanoshells made according to a disclosed embodiment. In FIG. 12a, the shell thickness of the silver nanoshells is about 45 nm while in FIG. 12b, the shell thickness of the silver nanoshells is about 50 nm.

Figure 13:
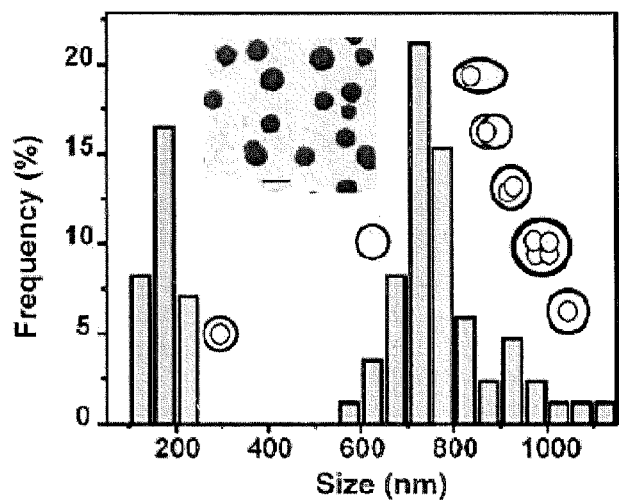

FIG. 13 is a graph showing the particle size distribution of gold nano-shells made according to Comparative Example 1 as well as schematic diagrams showing possible configurations of the gold nano-shells with the core particle(s) therein.

Figure 14:
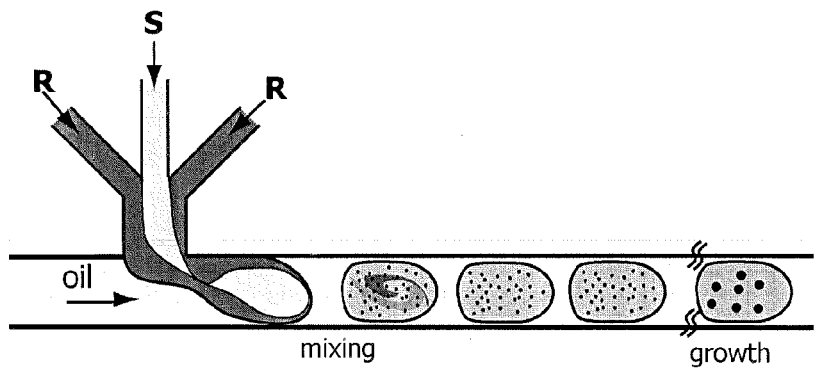

FIG. 14 is a schematic diagram of the two-phase approach to forming gold nano-shells according to Comparative Example 2.

Figure 15:
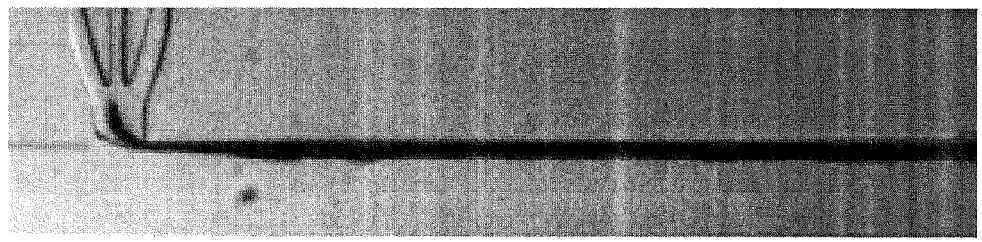

FIG. 15 is a photographic image of the micro-fluidic device showing the fouling of the micro-fluidic device according to Comparative Example 2.

DETAILED DESCRIPTION

Definitions

The following words and terms used herein shall have the meaning indicated:

The term "reactive" is to be interpreted broadly to include any chemical composition comprising components that are capable of reaction to form a particle. On the other hand, the term "non-reactive" is to be interpreted broadly to include any chemical composition comprising components that are substantially inert relative to each other, such that no reaction within the composition occurs. In the context of this specification, a non-reactive or inert material is non-reactive to a reactive material that produces particles.

The term "immiscible fluid" is to be interpreted broadly to refer to two or more mutually insoluble fluids present as separate phases. The mutually insoluble fluids tend to repel each other and any area of contact between each other is minimized.

The term "foam" refers to a multi-phase composition where a gaseous phase is present as dispersed pockets in a liquid phase or solid phase.

The terms "micro" or "microparticle" are to be interpreted broadly to, unless specified, relate to an average particle size of between about 1 µM to about 1000 µM. The particle size may refer to the diameter of the particles where they are substantially spherical. The particles may be non-spherical and the particle size range may refer to the equivalent diameter of the particles relative to spherical particles or may refer to a dimension (length, breadth, height or thickness) of the non-spherical particle. The term "sub-micron" as used herein refers to a size of less than 1 µm, specifically from about 1 nm to about 1 µm, inclusively.

The terms "nano", "nano-size" or "nanoparticle" are to be interpreted broadly to, unless specified, relate to an average particle size of less than about 1000 nm, particularly between about 1 nm to about 1000 nm. The particle size may refer to the diameter of the particles where they are substantially spherical. The particles may be non-spherical and the particle size range may refer to the equivalent diameter of the particles relative to spherical particles or may refer to a dimension (length, breadth, height or thickness) of the non-spherical particle.

The term "narrow particle size distribution" in the context of the specification typically refers to a group of particles which are substantially monodispersed with +/−5% deviation from the average particle diameter. Where the particles are non-spherical, the particle diameter refers to the equivalent diameter of the particles.

The term "microchamber", in the context of this specification, refers to an enclosed volume where the fluids are mixed and wherein the enclosed volume has dimensions in the micro-meter range.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DETAILED DISCLOSURE OF EMBODIMENTS

Exemplary, non-limiting embodiments of a method for synthesizing colloidal nanoparticles will now be disclosed.

In one embodiment, the method comprises the step of creating a reactive three-phase foam containing reactants therein for synthesizing the colloidal nanoparticles.

The creating step may comprise the step of mixing at least two fluids that are immiscible with each other to form a two-phase fluid flow.

The mixing step may comprise the step of mixing said fluids in a microchamber.

In one embodiment, the fluids are provided at substantially equal pressure when introduced into the microchamber. The substantially equal pressure may vary by no more than 10% from each other.

In another embodiment, one of the fluids is intermittently provided at a higher pressure relative to the other fluid when introduced into the microchamber.

The two fluids may be provided as inlet conduit streams in a micro-conduit. The inlet conduit streams may be introduced into the microchamber at about 30 degrees to about 150 degrees relative to a horizontal plane of the microchamber.

The creating step may further comprise the step of coating the two-phase fluid flow with a continuous phase to form a three-phase fluid flow.

In one embodiment, the two fluids that are immiscible with each other comprise an aqueous fluid and a gas fluid.

In one embodiment, the three phase fluid flow in the microchamber is in the laminar region, where $0.1 < Re < 1000$.

The two-phase fluid flow may contain the reactants therein to synthesize the colloidal nanoparticles.

The coating phase may comprise an oil fluid. The aqueous phase and gas phase may be immersed in the continuous oil phase.

In one embodiment, the ratio of the flow rate of the oil phase to the flow rate of the aqueous phase is from about 0.1 to about 2.0. In one embodiment, the ratio of the flow rate of the oil phase to the flow rate of the aqueous phase is 0.5.

In one embodiment, the flow rates of the oil phase and the aqueous phase are substantially constant.

The continuous phase may have a flow rate in the range of about 1 µL/min to about 60 µL/min, or about 5 µL/min to about 60 µL/min, or about 10 µL/min to about 60 µL/min, or about 15 µL/min to about 60 µL/min, or about 20 µL/min to about 60 µL/min, or about 30 µL/min to about 60 µL/min, or about 40 µL/min to about 60 µL/min, or about 50 µL/min to about 60 µL/min, or about 1 µL/min to about 50 µL/min, or about 1 µL/min to about 40 µL/min, or about 1 µL/min to about 30 µL/min, or about 1 µL/min to about 20 µL/min, or about 1 µL/min to about 15 µL/min, or about 1 µL/min to about 10 µL/min, or about 1 µL/min to about 5 µL/min.

The aqueous stream may have a flow rate in the range of about 0.1 µL/min to about 60 µL/min, or 1 µL/min to about 60 µL/min, or about 5 µL/min to about 60 µL/min, or about 10 µL/min to about 60 µL/min, or about 15 µL/min to about 60 µL/min, or about 20 µL/min to about 60 µL/min, or about 30 µL/min to about 60 µL/min, or about 40 µL/min to about 60 µL/min, or about 50 µL/min to about 60 µL/min, or about 0.1 µL/min to about 50 µL/min, or about 0.1 µL/min to about 40 µL/min, or about 0.1 µL/min to about 30 µL/min, or about 0.1 µL/min to about 20 µL/min, or about 0.1 µL/min to about 15 µL/min, or about 0.1 µL/min to about 10 µL/min, or about 0.1 µL/min to about 5 µL/min, or about 0.1 µL/min to about 1 µL/min.

The pressure of the gas may be in the range of about 34.5 kPa (5 psi) to about 344.7 kPa (50 psi), or about 68.9 kPa (10 psi) to about 344.7 kPa (50 psi), or about 103.4 kPa (15 psi) to about 344.7 kPa (50 psi), or about 137.9 kPa (20 psi) to about 344.7 kPa (50 psi), or about 172.4 kPa (25 psi) to about 344.7 kPa (50 psi), or about 206.8 kPa (30 psi) to about 344.7 kPa (50 psi), or about 241.3 kPa (35 psi) to about 344.7 kPa (50 psi), or about 275.8 kPa (40 psi) to about 344.7 kPa (50 psi), or about 310.3 kPa (45 psi) to about 344.7 kPa (50 psi), or about 34.5 kPa (5 psi) to about 310.3 kPa (45 psi), or about 34.5 kPa (5 psi) to about 275.8 kPa (40 psi), or about 34.5 kPa (5 psi) to about 241.3 kPa (35 psi), or about 34.5 kPa (5 psi) to about 206.8 kPa (30 psi), or about 34.5 kPa (5 psi) to about 172.4 kPa (25 psi), or about 34.5 kPa (5 psi) to about 137.9 kPa (20 psi), or about 34.5 kPa (5 psi) to about 103.4 kPa (15 psi), or about 34.5 kPa (5 psi) to about 68.9 kPa (10 psi). In one embodiment, the pressure of the gas is about 117.2 kPa (17 psi). The gas phase may comprise an inert gas.

The method further comprises the step of forming an ordered three-phase fluid flow comprising alternating aqueous phase and gas phase immersed in a continuous oil phase.

In one embodiment, the method comprises the step of providing seed nano-particles dispersed in the aqueous phase.

The synthesized colloidal nanoparticles may have a narrow particle size distribution.

Advantageously, the disclosed method provides a robust, reproducible and continuous method for synthesizing colloids which cannot be achieved by current prior art methods. Colloids are sub-micron particles that are substantially uniformly dispersed in a continuous phase. Colloidal synthesis requires the production of tightly controlled particle size distributions. Advantageously, the disclosed method achieves this object along with higher yield as compared to prior art colloidal synthesis methods. Advantageously, the disclosed method negates the need for further purification steps to separate the different sizes of particles.

In one embodiment, the disclosed method is used to synthesize gold-coated nanoparticles as described in the examples below. The nanoparticles may have a range of diameters selected from the group consisting of about 50 nm to about 500 nm, about 100 nm to about 500 nm, about 150 nm to about 500 nm, about 200 nm to about 500 nm, about 250 nm to about 500 nm, about 300 nm to about 500 nm, about 350 nm to about 500 nm, about 400 nm to about 500 nm, about 50 nm to about 400 nm, about 50 nm to about 350 nm, about 50 nm to about 300 nm, about 50 nm to about 250 nm, about 50 nm to about 200 nm, about 50 nm to about 150 nm, and about 50 nm to about 100 nm. Where the cross-sectional area of the particle is substantially non-spherical, the diameter may refer to the equivalent diameter of the particle, wherein said equivalent diameter is relative to a completely spherical diameter. In some embodiments, the cross-section of the particle is completely spherical and the equivalent diameter is equal to the actual diameter of the particle. In one embodiment, the nanoparticles may be nano-rods.

In one embodiment, the residence time of the reactive phase may be from about 1 second to about 10 minutes. In another embodiment, the residence time of the reactive phase may be from about 1 second to 60 seconds. Advantageously, the fluid flow in the continuous phase conduit is analytically tractable. Thus, if the mechanism of growth of the nanoparticles is known, the growth mechanism can be coupled with the residence time distribution to predict the particle size distribution. Advantageously, the nanoparticles produced by the disclosed method may have a narrow particle size distribution.

In one embodiment, a three-phase reactive foam containing reactants therein for synthesizing colloidal nanoparticles. In one embodiment, the three-phase reactive foam comprises an alternating aqueous phase and gas phase immersed in a continuous oil phase.

In one embodiment, there is provided a microreactor system for synthesizing colloidal nanoparticles comprising at least two inlet conduits containing fluids therein, at least two of said fluids being immiscible with each other; mixing means in fluid communication with and positioned downstream of said at least two inlet conduits and being configured to mix said immiscible fluids to form a two-phase fluid flow; a continuous phase conduit in fluid communication with and positioned downstream of said mixing means for coating said two-phase fluid flow and thereby producing a three-phase fluid flow; and an outlet conduit positioned downstream of said continuous phase conduit for releasing said three-phase fluid flow, wherein said three-phase fluid contains reactants for synthesizing the colloidal nanoparticles.

In the context of the specification, the mixing means refers to an enclosed volume where the fluids are mixed and wherein the enclosed volume has dimensions in the micro-meter range.

In the embodiment where the junction is a substantially T-shaped junction, the at least two inlet conduits join the mixing means at a junction about 30 degrees to about 150 degrees relative to a horizontal plane through the mixing means.

In one embodiment, the junction is a substantially Y-shaped junction. In this embodiment, the at least two inlet conduits join the mixing means at a junction of a range of angles relative to a horizontal plane through the radial axis of the mixing means. The range of angles may be selected from the group consisting of about 30 degrees to about 60 degrees, about 35 degrees to about 60 degrees, about 40 degrees to about 60 degrees, about 45 degrees to about 60 degrees, about 50 degrees to about 60 degrees, about 55 degrees to about 60 degrees, about 30 degrees to about 55 degrees, about 30 degrees to about 50 degrees, about 30 degrees to about 45 degrees, about 30 degrees to about 40 degrees, and about 30 degrees to about 35 degrees.

In one embodiment, the junction has a geometry of any combination as described above.

The at least two inlet conduits may be configured at an angle relative to each other in a range selected from the group consisting of about 10 degrees to about 90 degrees, about 20 degrees to about 90 degrees, about 30 degrees to about 90 degrees, about 40 degrees to about 90 degrees, about 50 degrees to about 90 degrees, about 60 degrees to about 90 degrees, about 70 degrees to about 90 degrees, about 80 degrees to about 90 degrees, about 10 degrees to about 80 degrees, about 10 degrees to about 70 degrees, about 10 degrees to about 60 degrees, about 10 degrees to about 50 degrees, about 10 degrees to about 40 degrees, about 10 degrees to about 30 degrees, and about 10 degrees to about 20 degrees.

The inlet conduits may have a range of diameters selected from the group consisting of about 75 μm to about 150 μm, about 100 μm to about 150 μm, about 125 μm to about 150 μm, about 75 μm to about 125 μm, and about 75 μm to about 100 μm. Where the cross-sectional area of the inlet conduit is substantially non-spherical, the diameter may refer to the equivalent diameter of the inlet conduit conduit, wherein said equivalent diameter is relative to a completely spherical diameter. In some embodiments, the cross-section of the inlet conduit is completely spherical and the equivalent diameter is equal to the actual diameter of the inlet conduit.

The continuous phase conduit may have a range of diameters selected from the group consisting of about 50 μm to about 500 μm, about 100 μm to about 500 μm, about 300 μm to about 500 μm, about 50 μm to about 300 μm, and about 50 μm to about 100 μm. Where the cross-sectional area of the continuous phase conduit is substantially non-spherical, the diameter may refer to the equivalent diameter of the continuous phase conduit, wherein said equivalent diameter is relative to a completely spherical diameter. In some embodiments, the cross-section of the continuous phase conduit is completely spherical and the equivalent diameter is equal to the actual diameter of the continuous phase conduit.

Advantageously, due to the dimensions of the continuous phase conduit and the inlet conduits, the immiscible fluids in the dispersed phase may be maintained in the laminar region. Laminar flow is measured by $$Re = \rho v d/\mu$$

wherein $\rho$ is the density of the fluid, $v$ is velocity of the fluid, $d$ is the diameter and $\mu$ is the viscosity of the fluid, and wherein $0.1 < Re < 1000$. The foam formation depends upon the interplay between the viscous forces, inertial forces and interfacial forces. Advantageously, controlled foams are formed when interfacial forces dominate the others, as is the case for small geometries of less than 1 mm in diameter, because interfacial forces are inversely proportional to the conduit dimension, and are significantly weakened above geometries of more than 1 mm in diameter.

The residence time of the reactive phase in the continuous phase conduit is reaction-dependent. Advantageously, the flow of the reactive phase in the continuous phase conduit is analytically tractable. Hence, if the reaction mechanism is known, it can be coupled with the residence time distribution to predict the particle size distribution. In one embodiment, the residence time of the reactive phase is about 1 second to about 10 mins. In another embodiment, the residence time of the reactive phase is about 1 second to about 60 seconds.

The total length of the continuous phase conduit may be dependent on the residence time of the reactive phase. In one embodiment, the total length of the continuous phase conduit may be about 15 cm to about 150 cm, or about 50 cm to about 150 cm, or about 100 cm to about 150 cm, or about 15 cm to about 100 cm, or about 15 cm to about 50 cm.

A continuous phase may be introduced into the continuous phase conduit. In one embodiment, the continuous phase is an ionic liquid. In another embodiment, the continuous phase is a hydrocarbon, non-polar solvent, or a hydrophobic liquid. Exemplified hydrocarbons may be hydrocarbon oil such as silicone oil, vegetable oil, mineral oil, synthetic oil, and synthetic oils grafted with halides. In one embodiment, the hydrocarbon oil may be injected into the continuous phase conduit at a continuous rate. Advantageously, the continuous phase surrounds and coats the dispersed phases, such that the reactive phase does not deposit or aggregate on the wall of the continuous phase conduit, thereby preventing fouling of the continuous phase conduit.

The fluids in the at least two inlet conduits may be at substantially equal pressure when introduced into the mixing means.

The continuous phase may be introduced into the conduit at a flow rate ($Q_{continuous}$) in the range of about 1 μL/min to about 60 μL/min, or about 5 μL/min to about 60 μL/min, or about 10 μL/min to about 60 μL/min, or about 15 μL/min to about 60 μL/min, or about 20 μL/min to about 60 μL/min, or about 30 µL/min to about 60 or about 40 µL/min to about 60 µL/min, or about 50 µL/min to about 60 µL/min, or about 1 µL/min to about 50 µL/min, or about 1 µL/min to about 40 µL/min, or about 1 µL/min to about 30 µL/min, or about 1 µL/min to about 20 µL/min, or about 1 µL/min to about 15 µL/min, or about 1 µL/min to about 10 or about 1 µL/min to about 5 µL/min.

An aqueous phase may be introduced into one of the at least two inlet conduits. The aqueous phase may be introduced continuously into the inlet conduit. The aqueous phase may be immiscible with the continuous phase. In one embodiment, the aqueous phase may be a reactive phase. In the embodiment where the aqueous phase is a reactive phase, more than one aqueous phase may be introduced, such that different reagents required for reaction may be added.

In one embodiment, the aqueous phase is injected at a constant flow rate ($Q_{dispersed}$). The aqueous may be introduced into the system at a flow rate in the range of about 1 µL/min to about 60 µL/min, or about 5 µL/min to about 60 µL/min, or about 10 µL/min to about 60 µL/min, or about 15 µL/min to about 60 µL/min, or about 20 µL/min to about 60 µL/min, or about 30 µL/min to about 60 µL/min, or about 40 µL/min to about 60 µL/min, or about 50 µL/min to about 60 µL/min, or about 1 µL/min to about 50 µL/min, or about 1 µL/min to about 40 µL/min, or about 1 µL/min to about 30 µL/min, or about 1 µL/min to about 20 µL/min, or about 1 µL/min to about 15 µL/min, or about 1 µL/min to about 10 µL/min, or about 1 µL/min to about 5 µL/min.

In one embodiment, the maximum total flow rate of the liquid phases ($Q_{continuous}+Q_{dispersed}$) is 60 µL/min. If the total flow rate exceeds 60 µL/min, delamination occurs due to the high pressure drop within the continuous phase conduit. In one embodiment, the minimum total flow rate of the liquid phases is 1.1 µL/min. In one embodiment, the ratio of the flow rate of the continuous phase to the flow rate of the dispersed aqueous phase ($Q_{continuous}:Q_{dispersed}$) is kept constant. In one embodiment, $Q_{continuous}:Q_{dispersed}$ is from about 0.1 to about 2.0. In one embodiment, $Q_{continuous}:Q_{dispersed}$ is maintained at 0.5. It should be noted that $Q_{continuous}:Q_{dispersed}$ may be kept constant, provided the maximum total flow rate of ($Q_{continuous}+Q_{dispersed}$) does not exceed 60 µL/min.

$Q_{continuous}:Q_{dispersed}$ may be chosen to cater to the desired configuration of alternating dispersed phases. For example, $Q_{continuous}:Q_{dispersed}$ in the range of about 0.1 to about 0.6 enables the formation of a tightly packed alternating dispersed phase. Alternatively, $Q_{continuous}:Q_{dispersed}$ in the range of about 0.6 to about 1.9 enables the formation of distinct coupled dispersed phases.

A gas phase may be introduced into one of the at least two inlet conduits. The gas phase may be introduced continuously into the inlet conduit. The gas phase may be immiscible with the continuous phase. The gas phase may also be immiscible with the aqueous phase. In one embodiment, the gas phase is a reactive phase. In this embodiment, the gas may be a mixture of inert gases and/or of reactive reducing gases. The inert gases may be, although not limited to, nitrogen, carbon dioxide, and helium. The reactive gases may be, although not limited to, carbon monoxide, phosphine, hydrogen, and ammonia. In one embodiment, the gas phase is a non-reactive phase.

Advantageously, at least one dispersed phase is a gaseous phase. Advantageously, the gas phase may aid in the prevention of reagent buildup at the junction, thereby preventing fouling of the system.

In one embodiment, the gas phase is pumped into the system at a constant pressure. The gas may be pumped into the system by a pressurized cylinder. The gas may be pumped into the system at a pressure in the range of about 34.5 kPa (5 psi) to about 172.4 kPa (25 psi), or about 68.9 kPa (10 psi) to about 172.4 kPa (25 psi), or about 103.4 kPa (15 psi) to about 172.4 kPa (25 psi), or about 137.9 kPa (20 psi) to about 172.4 kPa (25 psi), or about 34.5 kPa (5 psi) to about 137.9 kPa (20 psi), or about 34.5 kPa (5 psi) to about 103.4 kPa (15 psi), or about 34.5 kPa (5 psi) to about 68.9 kPa (10 psi). Generally, the higher the gas pressure, the larger the gaseous compartment in the continuous phase conduit. In one embodiment, the gas may be introduced into the system at about 117.2 kPa (17 psi).

The aqueous phase and the gas phase converge and meet the continuous phase at the junction. Due to the interplay between flow properties of the dispersed phases, the cross-sectional diameter of the continuous phase conduit and the angles of the inlet conduits, foam of alternating gaseous and aqueous phase may be produced at the junction by a block-pinch mechanism. When the gas phase flows through the continuous phase conduit, it is pinched off at one corner of the junction when the advancing interface of the aqueous phase flows into the continuous phase conduit. As the aqueous phase flows through and travels down the continuous phase conduit, the aqueous phase is pinched off at its other end by the advancing interface of the next flow of gaseous phase. Accordingly, foam of alternating gaseous and aqueous phases may be produced.

In one embodiment, the aqueous phase is reactive and the gas phase is non-reactive. Advantageously, in this embodiment, the reactive dispersed phase and the non-reactive dispersed phase are alternated. In yet another embodiment, both the aqueous phase and the gas phase are reactive. Each reactive compartment may thus be viewed as an individual batch reactor. As such, reactions may be controlled with increased precision.

The system may comprise an outlet downstream of the continuous phase conduit. The outlet may be in fluid communication with a collection vessel to collect the products from the reactive phase.

The collection vessel may be analyzed by any known suitable method to determine the properties of the products collected.

In one embodiment, there is provided a microreactor comprising: at least two inlet conduits for containing fluids therein in which at least two of said fluids are immiscible with each other; mixing means in fluid communication with and positioned downstream of said at least two inlet conduits and being configured to mix said immiscible fluids to form a two-phase fluid flow; a continuous phase conduit in fluid communication with and positioned downstream of said mixing means for coating said two-phase fluid flow and thereby producing a three-phase fluid flow; and an outlet conduit positioned downstream of said continuous phase conduit for releasing said three-phase fluid flow.

The microreactor may be fabricated on a wafer block using techniques which include photolithography, physical or chemical etching, hot embossing, and reaction-injection molding. In one embodiment, the soft lithography technique is used to fabricate the microreactor. Wafer blocks used in this embodiment may be made from silicone, such as poly(dimethyl siloxane), glass or polymers. Advantageously, soft lithography enables the micro-fabrication of patterns onto non-planar surfaces and also enables compatibility with polymers, metals and ceramics. In another embodiment, laser micromachining is used to fabricate the microreactor. Wafer blocks used in this embodiment may be made from glass or plastic.

Advantageously, the microreactor may be fabricated to be capable of handling reactions occurring at low to medium temperature ranges, such as from room temperature of about 25° C. to about 200° C. Advantageously, the microreactor may also be capable of handling reactions, such as photochemical based synthesis processes, occurring at elevated temperatures from about 200° C. to about 500° C.

DETAILED DESCRIPTION OF DRAWINGS

Figure 1:
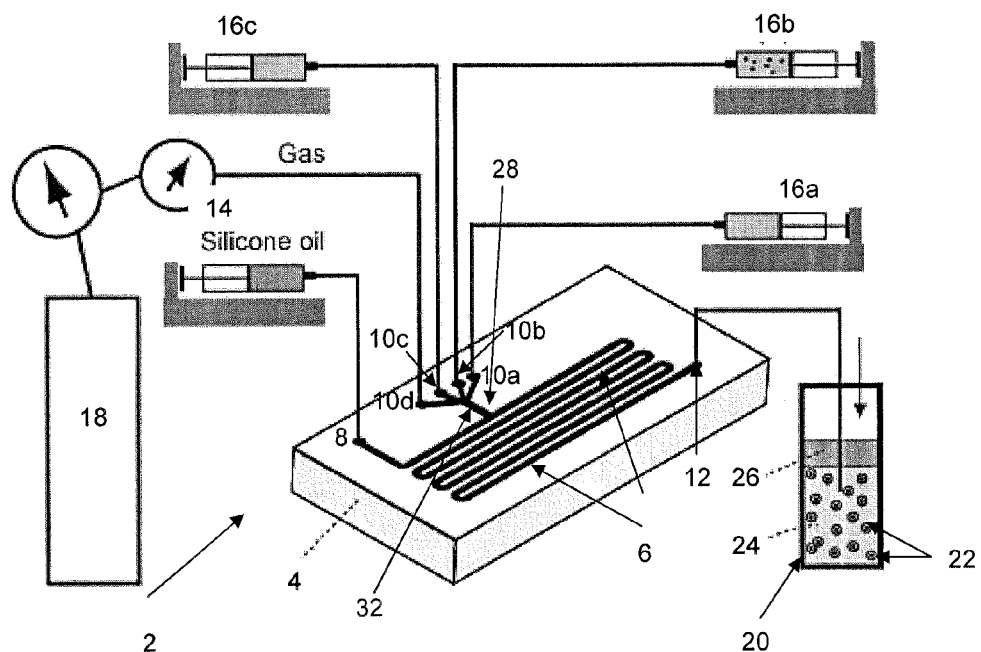
FIG. 1 is a schematic diagram of the micro-fluidic system for synthesizing nanoparticles according to one embodiment.
Figure 2:
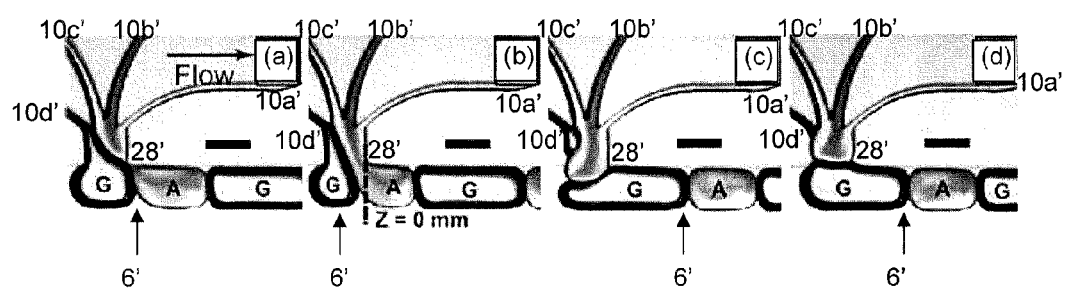
FIG. 2a to FIG. 2d are a series of stereomicroscope images showing the breakup and formation of composite foams at the T-junction. All scale bars represent 300 μM.

Referring to FIG. 1, there is provided a schematic diagram of a micro-fluidic system 2 according to one disclosed embodiment. The micro-fluidic system 2 is made up of a micro-fluidic device 4 in which a continuous phase conduit in the form of a continuous and winding micro-channel 6 is molded therein. The micro-channel 6 is then irreversibly bonded to a glass slide (not shown) pre-coated with a thin layer of the same material as the micro-fluidic device 4 after air plasma treatment. Inlet holes (8,10a,10b,10c,10d) and an outlet hole 12 are punched into the micro-fluidic device 4. The inlet holes (10a,10b,10c,10d) leads to respective inlet conduits for introducing respective fluids, at least two of which are immiscible with each other, into a mixing means such as a microchamber 32. The microchamber 32 is in fluid communication with and positioned downstream of the inlet conduits that lead from inlet holes (10a,10b,10c,10d) and is configured to mix the at least two immiscible fluids to form a two-phase fluid flow. The microchamber 32 joins the micro-channel 6 at a T-junction 28 while inlet hole 8 defines the start of the micro-channel 6 and introduces a continuous phase into the micro-channel which will form the third phase in the micro-channel 6. Hence, the micro-channel 6 is in fluid communication with and positioned downstream of the microchamber 32. Inlet hole 8 is in fluid communication with a syringe 14 for introducing a non-polar liquid such as oil into the micro-channel 6. Inlet holes (10a,10b,10c) are connected to respective syringes (16a,16b,16c) for introducing respective aqueous liquids into the micro-channel 6. The aqueous liquids are immiscible with the non-polar liquid such that the aqueous liquids combine together to form a 'capsule'-like cell in the non-polar liquid as shown in FIG. 2a (as denoted by the alphabet "A"). A gas supply unit 18 then introduces a gas into the micro-channel 6 through inlet 10d. Similarly to the aqueous liquids, the gas forms a "capsule"-like cell in the non-polar liquid as shown in FIG. 2a (as denoted by the alphabet "G"). The aqueous liquids and gas fluid are immiscible with each other. The non-polar liquid forms a continuous phase in the micro-channel 6 while the aqueous cell and gas cell form respective dispersed phases in the non-polar liquid. Hence, the non-polar liquid serves to coat the two-phase fluid flow (made up of the aqueous fluids and gas fluid) to thereby produce a three-phase fluid flow.

The aqueous liquids may be reactants and/or may contain seed particles for the synthesis of nano-shells or nano-particles. As the reactants (and/or seed particles) flow through the micro-channel 6 and exit through an outlet conduit positioned downstream of the micro-channel 6. The outlet conduit is in fluid communication with an outlet 12 which then leads to a collection vial 20. In the collection vial 20, the formed nano-shells or nano-particles 22 are suspended in the aqueous phase 24. The non-polar phase 26 is on top of the aqueous phase 24 due to its immiscibility with the aqueous phase 24. Similarly, the gas that is introduced from gas supply unit 18 passes through the micro-channel 6 but is lost to the environment after passing through the outlet hole 12.

Referring to FIGS. 2a to 2d, there is shown a series of stereomicroscope images showing the breakup and formation of "capsule"-like cells or composite foams at the T-junction 28'. Like reference numerals are used to denote technical features that are similar to those in FIG. 1 but with an additional prime (') symbol. A gas such as nitrogen gas is introduced via inlet 10d' into one arm of the micro-fluidic T-junction 28' while aqueous reactants such as those described in FIG. 1 above are introduced via inlet holes (10a',10b',10c') into the same arm of the micro-fluidic T-junction 28' as the gas. A non-polar fluid such as oil (not shown) is then introduced through the other arm of the micro-fluidic T-junction 28'. The gas also serves to periodically clear reactants from the T-junction 28', thereby preventing reactant build-up and nano-particle deposition that occurs when laminar fluid streams are left undisturbed.

Figure 3:
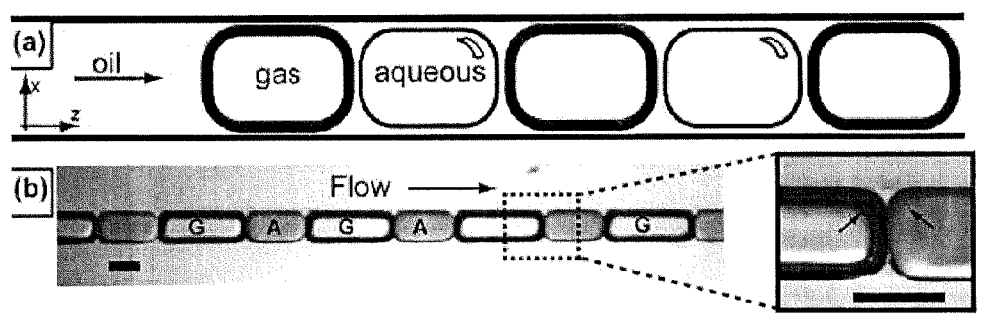
FIG. 3a is a schematic diagram of the flowing composite foam showing an alternating train of gas and aqueous liquid foam cells flowing through a continuous oil stream according to one embodiment.
FIG. 3b is a stereomicroscope image of the composite foam of FIG. 3a with the inset showing a magnified view of the gas (G)-aqueous (A) interface. All scale bars represent 300 μm.

At low volumetric oil flow rates relative to the aqueous stream, laminar flow conditions are created in the micro-channel 6' such that alternating gas and aqueous liquid cells are pinched off at the T-junction 28' and assemble downstream to form the "capsule"-like cells denoted by "G" and "A" respectively. As the "capsule"-like cells flow through the thin oil film, an ordered foam lattice as shown in FIG. 3a and FIG. 3b is formed in the micro-channel 6'. Minute differences in surface roughness between opposite micro-channel walls (due to micro-fabrication tolerances) and small differences in curvature of the fluid interfaces break the symmetry of the velocity field within each cell, and cause rapid chaotic mixing of the contents. The mixing patterns within the aqueous liquid cells are extremely robust, and display little cell-to-cell variation at any given downstream location. In situ foam generation therefore enables controllable and reproducible reagent dispensing and rapid chaotic mixing.

Referring to FIG. 3a and FIG. 3b, there is shown an ordered foam lattice of alternating gas ("G") and aqueous liquid ("A") cells flowing in a thin oil film. The inset of FIG. 3b shows a magnified view of the gas-aqueous interface. The arrows in the inset clearly define a sharp plateau border between the gas and aqueous liquid cells. The overall foam structure resembles the compact 'bamboo' structures observed in confined cylindrical foams. Ordered micro-fluidic composite foams possess a unique set of structural and functional features that make them attractive for processing specialty materials of micron and sub-micron sizes. As can be seen, the gas and aqueous liquid cells are of identical sizes with respect to each other. The aqueous liquid cells serve as individual reaction "flasks" and are effectively isolated from other reactant-filled cells and the walls of the micro-channel during their transit through the micro-channel. As the aqueous liquid cell moves through the micro-channel, the reactants and/or seed particles present in the aqueous liquid cell start to react. Based on the residence time of the aqueous liquid cell in the micro-channels, a desired product(s) such as a nano-shell(s) or nano-particle(s) can be formed in each aqueous liquid cell when the aqueous liquid cell reaches the end of the micro-channel. Hence, the reaction in each aqueous liquid cell occurs independently of each other and since there is no contact with the micro-channel walls, the aggregation and deposition of the contents of the aqueous liquid cells on the micro-channels walls are effectively minimized.

Figure 4:
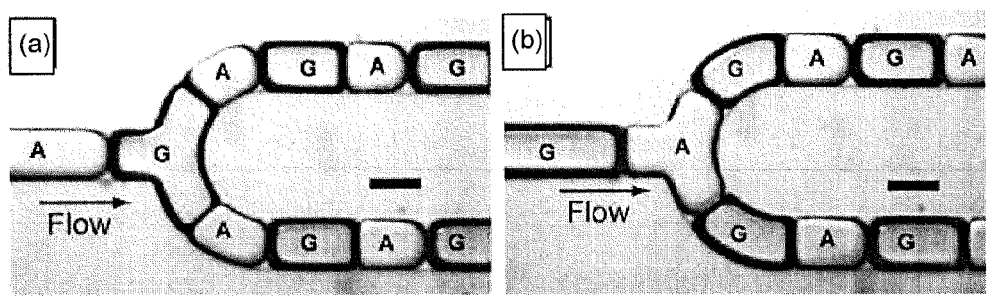
FIG. 4a and FIG. 4b are stereomicroscope images of the splitting of foam cells into equal-sized daughter cells at a bifurcation. All scale bars represent 300 μm.

Referring to FIG. 4a and FIG. 4b, there are shown stereomicroscope images of splitting of the gas and aqueous liquid foam cells, respectively, into equal-sized daughter cells at a bifurcation. This shows that such foams have the potential to perform elementary "digital" operations such as cell splitting and bifurcation in a micro-fluidic network. Hence, a potential application of this property of the foam cells is in autonomous logic-based multistep chemical processing operations.

Figure 5A:
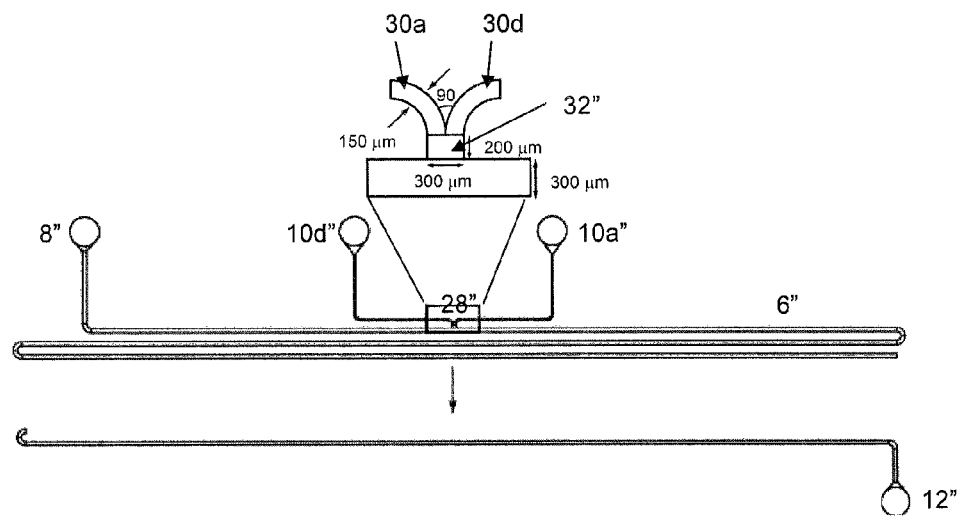
FIG. 5a is a schematic diagram showing the detailed design of the T junction geometry with two inlet conduit holes for formation of the composite foams.

Referring to FIG. 5a, there is shown a schematic diagram of the micro-channel 6" having the T-junction 28" geometry, inlet holes (8",10a",10d") and outlet hole 12". For simplicity, inlet holes 10b and 10c referred in FIG. 1 have been removed. Like reference numerals are used to denote technical features that are similar to those in FIG. 1 but with an additional double prime (") symbol. As can be seen from the inset of FIG. 5a, the diameter of the micro-channel 6" is 300 microns. The two inlet holes (10a", 10d") are disposed at an angle of 90° with respect to each other and the diameter of the micro-channels (30a,30d) that lead off directly from the inlet holes (10a",10d") is 150 microns. The two micro-channels (30a, 30d) meet at a microchamber 32", having a length of 300 microns and width of 200 microns. The microchamber 32" forms an arm of the T-junction 28" while the part of the micro-channel that leads from the inlet hole 8" to the T-junction 28" forms the other arm of the T-junction 28". At the T-junction 28", as described above, the alternating foam cells of gas and aqueous liquid are formed which then flow in the oil film in the micro-channel 6" until they reach the outlet hole 12" where the gas is released into the environment and the oil and the aqueous suspension containing the products is collected.

Figure 5B:
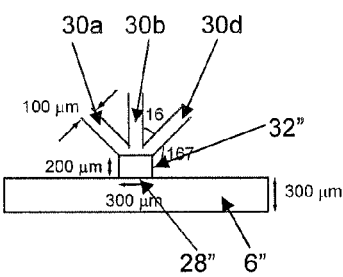
FIG. 5b and FIG. 5c are representative diagrams of the T-junction with three and four inlet conduit holes, respectively, that can be used to form composite foams.

FIG. 5b is an example of a T-junction 28" geometry with three inlet holes leading to three micro-channels (30a,30b, 30d) that leads into the microchamber 32". The respective angles between the micro-channels (30a,30b,30d), diameter of the micro-channels (30a,30b,30d), length and width of the collection point 32 and diameter of the micro-channel 6" are shown.

Figure 5C:
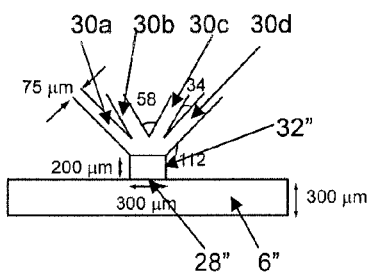

FIG. 5c is an example of a T-junction 28" geometry with four inlet holes leading to four micro-channels (30a,30b,30c, 30d) that leads into the microchamber 32". The respective angles between the micro-channels (30b,30c,30d), diameter of the micro-channels (30a,30b,30c,30d), length and width of the microchamber 32" and diameter of the micro-channel 6" are shown.

EXAMPLES

Non-limiting examples of the invention and comparative examples will be further described in greater detail by reference to specific Examples, which should not be construed as in any way limiting the scope of the invention.

Micro-Fabrication

Micro-fluidic device patterns were fabricated onto silicon wafers by standard photolithography using negative photoresist SU-8 2050 (obtained from Dow Corning of Michigan of the United States of America). The micro-fluidic device 2 was made in poly(dimethyl siloxane) (PDMS) (obtained from Dow Corning of Michigan of the United States of America) using the soft lithography technique. Briefly, PDMS was molded onto the SU-8 masters at 70° C. for 4 hours, peeled, cut and cleaned. The inlet and outlet holes (8,10a,10b,10c, 10d,12) of 1/16-in. o.d. were punched into the device which was then sealed to a glass slide pre-coated with a thin layer of PDMS after 35 seconds air plasma treatment. The micro-channel 6 has a rectangular cross-section and is 300 μm wide and ~155 μm deep with a length of 45 cm.

Micro-Fluidic Device Setup and Operation

The experimental set-up of the micro-fluidic system 2 of FIG. 1 was used for all of the examples herein. Syringe pump 14 was used to deliver silicone oil (Dow Corning DC50, viscosity 10 cSt, of Michigan of the United States of America) through inlet hole 8 to the micro-fluidic device 4. Syringe pumps (16a,16b,16c) were used to deliver reactant solutions and/or seed particles to the micro-fluidic device 4 as will be explained in each example below. Nitrogen gas was introduced from gas supply unit 18 which is a cylinder equipped with a two-stage pressure regulator through circular PEEK tubings (60 microns, 1.5 m long) leading into the on-chip gas inlet 10d.

All syringe pumps (14,16a,16b,16c) were obtained from Harvard Apparatus PHD 2000 from Instech Laboratories, Inc. of Pennsylvania of the United States of America.

Sample Collection and Analysis

The outlet hole 12 from the micro-fluidic device 4 was connected via fluoropolymer (FEP) tubing to a collection vial 20 in the form of a 2 mL centrifuge tube. Approximately 1 mL of the aqueous sample was collected in the tube for every experimental condition. The oil formed a layer on the surface of the collected aqueous fluid while the gas simply escaped into the ambient environment. The oil layer was carefully decanted and the aqueous fluid samples containing the requisite product were analysed with a UV-vis spectrometer (UV-2450 of Shimadzu of Japan). The samples were further purified by repeated centrifugation and redispersion in deionized water steps. A drop of this sample was placed onto a 200 mesh formwar protected copper grid and allowed to dry overnight. The copper grid was then analyzed using either TEM (JEOL 2010, accelerating voltage 200 kV, of JOEL Ltd, of Japan) or FESEM (JEOL JSM-6700f, accelerating voltage 4-25 kV, of JOEL Ltd, of Japan). Several images were taken at different locations on the grid and the particle size was found by manually measuring the diameter of at least 250 particles from several electron microscopy images.

Example 1

The micro-fluidic system set-up of FIG. 1 is used to form metallodielectric gold nano-shells which comprise a silica nano-particle core encased within a gold shell of tunable thickness. Here, nano-shell fabrication involves aqueous-based electro-less plating of nanometer-scale multi-crystalline gold films onto silica nano-particle surfaces (diameter d=50-200 nm) that have been pre-seeded with small gold nano-particles (diameter d=2-5 nm). In this method, gold nano-particle seeds on the silica particles serve as catalytic sites for the reduction of aqueous $Au^{[3+]}$ to $Au^{[0]}$ by reducing agents such as hydroxylamine, formaldehyde and so on.

Based on FIG. 1, in addition to the introduction of silicone oil and nitrogen gas as mentioned above, an aqueous mixture of gold-seeded silica particles and gold plating solution (hereafter denoted by "S") was introduced into the micro-fluidic device 4 via syringe 16b to inlet hole 10b while an aqueous reducing agent solution (hereafter denoted by "R") was introduced to the micro-fluidic device 4 via syringes (16a,16c) to inlet holes (10a,10c). The gold plating solution was aged gold hydroxide (249 mg (1.8 mM) of potassium carbonate (obtained from Sigma-Aldrich Co. Ltd., of Singapore) in 1 L (0.435 mM) of hydrogen tetrachloroaurate (III) trihydrate solution (obtained from Sigma-Aldrich Co. Ltd., of Singapore)). The $[Au^{3+}]$ in plating solution and corresponding volume fraction of gold-seeded silica particles ($f_S$) in S were varied to obtain nanoshells of varying thickness, as will be explained further below. Freshly prepared hydroxyl amine hydrochloride (4 mM, obtained from Aldrich Chemical Co., of Singapore) was used as the reducing agent solution. Flow rates of the individual streams of S and R are maintained at 8 μl/min and 2 μl/min each respectively and the volumetric flow ratio of the aqueous reagents (S and R) to oil entering the micro-channel 6 is maintained at 2. The nitrogen gas pressure is kept constant at 17 psi.

Figure 6:
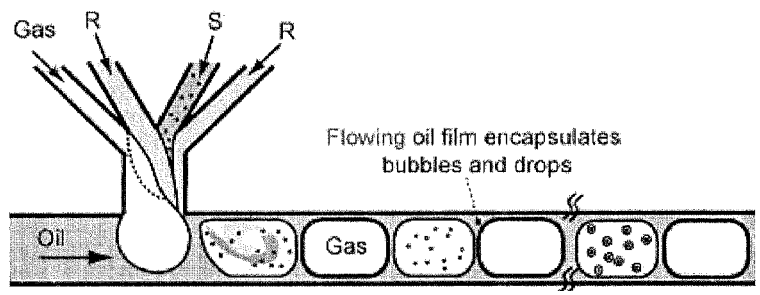
FIG. 6 is a conceptual schematic diagram of the composite foam showing an alternating train of gas and aqueous liquid foam cells flowing through a continuous oil stream according to one embodiment, in which nanoparticles are formed in the aqueous liquid foam cell.

The aqueous solutions (S and R) then enter the microchannel 6 via the T-junction 28 and form a "capsule"-like cell that alternates with the gas cell as shown in FIG. 6. The flowing foam cells spend about 120 s in the long microchannel 6 downstream of the T-junction 28 such that ultimately, each aqueous foam cell is made up of a suspension of gold nano-shells in the aqueous solution mixture. The aqueous foam cells containing the gold nano-shells suspension subsequently enter a collection vial 20 where the gas escapes, and the aqueous phase 24 and oil phase 26 spontaneously form two immiscible fluid layers.

Three sets of experiments were carried out in this example in order to obtain gold nano-shells of varying thickness from 10 nm, 20 nm, 30 nm and 40 nm. The results of this example are shown in FIGS. 7(a) to 7(e) and in FIG. 8(a) to FIG. 8(d).

Figure 7:
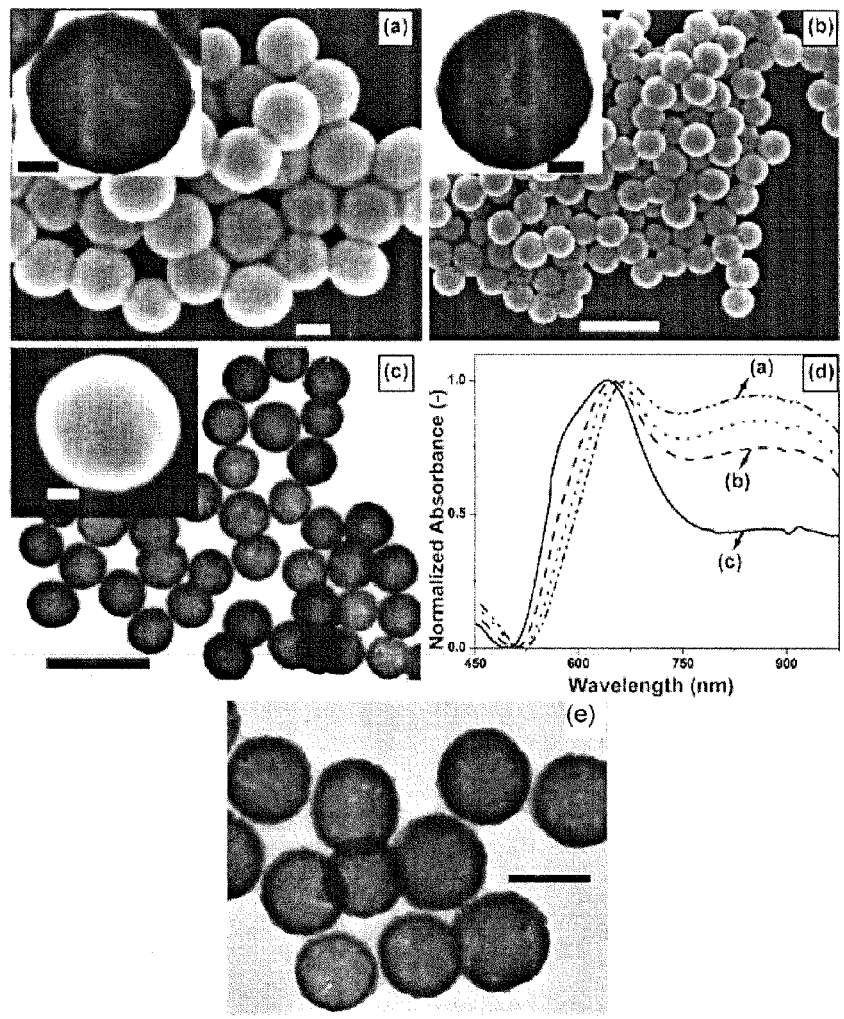
FIG. 7a shows a Scanning Electron Microscope (SEM) image of a population of complete smooth gold nanoshells with shell thickness of about 20 nm. The scale bar corresponds to 100 nm. The inset is a Transmission Electron Microscope (TEM) image in which a single gold nanoshell is magnified. The scale bar showing 50 nm.
FIG. 7b shows a SEM image of a population of complete smooth gold nanoshells with shell thickness of about 30 nm. The scale bar corresponds to 500 nm. The inset shows a magnified TEM image of a single gold nanoshell with the scale bar showing 50 nm.
FIG. 7c shows a TEM image of a population of complete smooth gold nanoshells with shell thickness of about 40 nm. The scale bar corresponds to 500 nm. The inset shows a magnified SEM image of a single gold nanoshell with the scale bar showing 50 nm.
FIG. 7d is a graph of the corresponding UV-visible absorbance spectra of the gold nanoshells of FIG. 7a to FIG. 7c.
FIG. 7(e) is a TEM image of gold nano-shells in which the thickness of the shell is 10 nm. The scale bar corresponds to 200 nm.

FIG. 7(a) is a SEM image of gold nano-shells in which the thickness of the shell is 20 nm. These nano-shells were obtained at a $[Au^{3+}]$ of 0.42 mM and $f_S$ of $3.9 \times 10^{-3}$%. FIG. 7(b) is a SEM image of gold nano-shells in which the thickness of the shell is 30 nm. These nano-shells were obtained at a $[Au^{3+}]$ of 0.43 mM and $f_S$ of $1.96 \times 10^{-3}$% %. FIG. 7(c) is a TEM image of gold nano-shells in which the thickness of the shell is 40 nm. These nano-shells were obtained at a $[Au^{3+}]$ of 0.43 mM and $f_S$ of $1.47 \times 10^{-3}$%. FIG. 7d is the corresponding UV-visible absorbance spectra of the gold nano-shells of FIG. 7(a) to FIG. 7(c). The unlabelled line in FIG. 7(d) corresponds to a shell thickness of about 25 nm, which was made using a $[Au^{3+}]$ of 0.422 mM and a $f_S$ of $2.94 \times 10^{-3}$%. FIG. 7(e) is a TEM image of gold nano-shells in which the thickness of the shell is 10 nm. These nano-shells were obtained at a $[Au^{3+}]$ of 0.41 mM and $f_S$ of $4.9 \times 10{-3}$%. FIG. 7(d) clearly indicates the presence of two spectral resonance peaks, with a sharp lower wavelength peak at ~650 nm that blue-shifted with increasing shell thickness (from (a) to (c)), and a broad shouldered peak at 900 nm. These peaks may be thought of as resulting from a hybridization of inner and outer shell plasmons.

Figure 8:
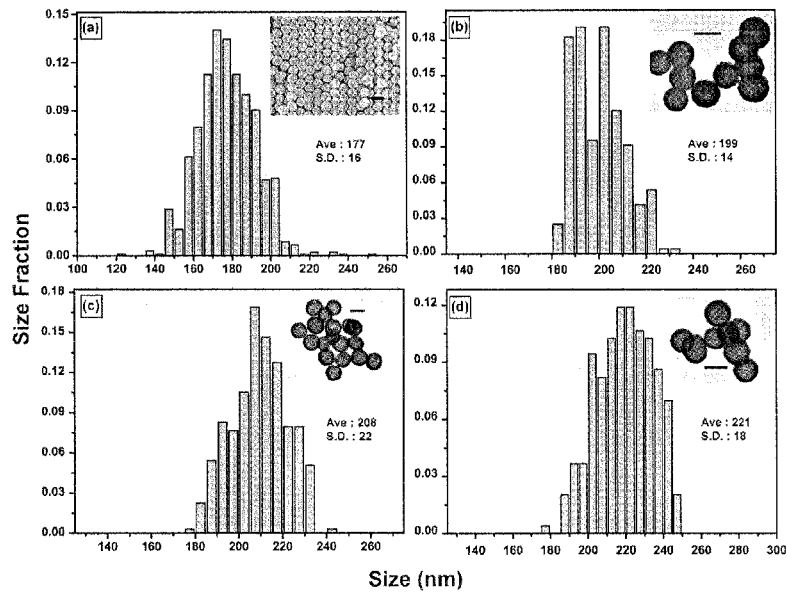
FIG. 8a shows the particle size distribution of original silica particles. The inset shows a SEM image of a representative particle population. Scale bar represents 200 nm.
FIG. 8b shows the particle size distribution of gold coated silica particles with average shell thickness of about 20 nm. The inset shows a TEM image of a representative particle population. Scale bar represents 200 nm.
FIG. 8c shows the particle size distribution of gold coated silica particles with average shell thickness of about 30 nm. The inset shows a TEM image of a representative particle population. Scale bar represents 200 nm.
FIG. 8d shows the particle size distribution of gold coated silica particles with average shell thickness of about 40 nm.

FIG. 8(a) shows the particle size distribution of original silica particles while FIG. 8(b) to FIG. 8(d) show the particle size distribution of the particle population synthesized in this Example. The particle size distribution data of these figures were measured from the electron microscope. FIG. 8(b) shows the particle size distribution of gold coated silica particles with an average shell thickness of 20 nm. FIG. 8(c) shows the particle size distribution of gold coated silica particles with an average shell thickness of 30 nm. FIG. 8(d) shows the particle size distribution of gold coated silica particles with an average shell thickness of 40 nm. As can be seen, the gold coated silica particles obtained from this Example are uniformly sized and show relatively tight, unimodal particle size distribution.

Example 2

Dielectric nano-particles decorated with small metallic islands are of considerable interest as substrates for a wide range of biological sensing applications. The optical properties of such particles depend on size and spacing of the metallic islands. Interactions between surface plasmons of neighboring islands can strongly affect the positions of the optical resonances.

In this Example, tightly controlled populations of silica nano-particles decorated with gold nano-islands of various sizes (FIGS. 9(a) to 9(d), FIG. 9(f) to FIG. 9(h)) were synthesized while operating in the gold-limited region of the $f_S$-$[Au^{3+}]$ parameter space. The process conditions and reagents of Example 1 are followed here, but with the $[Au^{3+}]$ and $f_S$ varied as mentioned further below. FIG. 9(a) shows the TEM image of a gold-seeded silica particle solution showing 3 nm gold seeds (dark spots) on silica particles. The average spacing between adjacent seeds is about 7 nm. The spectra of these particles exhibit the base scattering spectra with a slight shoulder at 520 nm (refer to FIG. 9(e)). FIG. 9(b) (TEM image) and FIG. 9(f) (SEM image) show the growth of the gold seeds from 3 nm in FIG. 9(a) to about 10 nm with a spectral peak of 640 nm (refer to FIG. 9(e)). Here, the $[Au^{3+}]$ used was 0.29 mM and $f_S$ in S was of $1.2 \times 10^{-2}$%, FIG. 9(c) (TEM image) and FIG. 9(g) (SEM image) show the growth of the gold seeds from 3 nm in FIG. 9(a) to about 35 nm with a spectral peak of 725 nm (refer to FIG. 9(e)). Here, the $[Au^{3+}]$ used was 0.39 mM and $f_S$ in S was $3.8 \times 10^{-3}$%. FIG. 9(d) is an image showing the further growth and coalescence of the flattened nano-islands. The particles exhibit a broad peak between 800 and 900 nm due to the presence of anisotropic islands of different sizes. Here, the $[Au^{3+}]$ used was 0.4 mM and $f_S$ in S was $3.4 \times 10^{-3}$%.

As can be seen from these figures and as observed by electron microscopy, analysis of these particles also indicates a possible mechanism of nano-shell growth, in which growing seed particles first coalesce into large, irregularly shaped islands (refer to FIG. 9(b) and FIG. 9(c)) that eventually coalesce to yield a complete shell as shown in FIG. 9(d). The combined effect of anisotropy in island shape and localized surface plasmon interactions between islands is to red-shift the absorption maximum (see FIG. 9(e)), with further peak broadening due to wide island size distributions.

This is also seen in marked variations in the color of the nanoparticle suspensions in which FIG. 10(a) is a photographic image of a gold-seeded silica particle solution which is brownish in colour; FIG. 10(b) is a photographic image of silica particles decorated with 10 nm gold nano-islands which is purple in colour; FIG. 10(c) is a photographic image of silica particles decorated with 35 nm gold nano-islands which is dark blue in colour; FIG. 10(d) is a photographic image of silica particles with nearly coalesced gold nano-islands which is slightly blue in colour; and FIG. 10(e) is a photographic image of completely smooth gold nano-shells with a thickness of 30 nm which is also slightly blue in colour.

Example 3

The micro-fluidic system set-up of FIG. 1 was used to form metallic nano-crystals of tailored shape and size. Here, rod-shaped gold nano-crystal dispersions were formed. In this synthesis protocol, small, nearly spherical gold nano-particle seeds (size <2 nm) were grown into rod-shaped nano-crystals by the reduction of tri-valent gold ($Au^{[3+]}$) to zero-valent gold ($Au^{[0]}$) with L-(+) ascorbic acid (AA, obtained from Alfa Aesar Co. Inc., Singapore) in the presence of cationic surfactant (cetyl trimethylammonium bromide (CTAB, obtained from Sigma-Aldrich Co. Ltd., Singapore) and small amounts of dissolved silver nitrate ($Ag^{[+]}$, 99.9% of Ag obtained from Strem Chemicals, Singapore). 18MΩ-cm ultrapure deionised water was used for all experiments and all reagents were used without further purification. Pre-mixed $Au^{[3+]}$, $Ag^{[+]}$ and CTAB solution, an aqueous solution of AA and seed suspension form the three reagent streams in this example which are fed separately through individual inlets (10a,10b,10c) into one arm of the T-junction 28. The gold nanoparticle seed suspension was fed through syringe 16a, the mixture of CTAB (4 mL of 250 mM), gold salt solution (4 mL of 1.25 mM) and varying volumes of silver nitrate solution (0.05 mL to 0.25 mL of 4 mM, varied in steps of 0.05 mL) was fed through syringe 16b and 5.16 mM of ascorbic acid was fed through syringe 16c. The flow rate of the aqueous stream was 9.3 µL/min, the flow rate of the oil stream was 1.4 µL/min and the gas pressure was 15 psi.

As seen in FIG. 11(a) and FIG. 11(b), excellent shape, size and spectral tunability of the gold nano-rods dispersions can be achieved by manipulating reagent concentrations and feed rates of the individual aqueous streams entering the micro-fluidic device. The different between FIG. 11(a) and FIG. 11(b) is in the silver nitrate volume used. In FIG. 11(a) the volume of silver nitrate used was 0.2 mL while the volume of silver nitrate used in FIG. 11(b) was 0.25 mL. Due to this difference, the aspect ratio of the gold nanorods in FIG. 11a is about 5 while the aspect ratio of the gold nanorods in FIG. 11b is about 4.

Metallic nano-crystals of tailored shape and size are important components in several nascent but promising applications ranging from nanomedicine, sensors, and chemical catalysis to nanoscale optical circuits and plasmonic invisibility cloaks.

Example 4

The micro-fluidic system set-up of FIG. 1 is used to form metallodielectric silver nano-shells which comprise a silica nano-particle core encased within a silver shell of tunable thickness. The metallodielectric silver nano-shells can be used as sensors. Here, nano-shell fabrication involves aqueous-based electro-less plating of silver films onto silica nano-particle surfaces that have been pre-seeded with small gold nano-particles (diameter d=2-5 nm).

Based on FIG. 1, in addition to the introduction of silicone oil and nitrogen gas as mentioned above, an aqueous mixture of freshly prepared silver nitrate solution (0.15 mM) and seeded silica particles were introduced into the micro-fluidic device 4 via syringe 16b to inlet hole 10b while a reducing agent such as formaldehyde (33 mM, 99% from Aldrich Chemical Co., Singapore) was introduced to the micro-fluidic device 4 via syringe 16a to inlet hole 10a. A second reducing agent such as ammonium hydroxide (37 mM, 28% $NH_3$ in water, 99.99+%, obtained from Aldrich Chemical Co., Singapore) was introduced to the micro-fluidic device 4 via syringe 16c to inlet hole 10c. All chemicals were used as obtained without any further purification. Ultrapure water (18 MΩ-cm, ELGA, Singapore) and glassware washed in aqua regia and rinsed thoroughly in water were used for experiments. The flow rate of the aqueous stream was 16 µL/min, the flow rate of the oil stream was 8 µL/min and the gas pressure was 13.5 psi.

Referring to FIG. 12(a) and FIG. 12(b), uniformly sized silver nano-shells are formed. The concentration of seeded silica used was $2\times10^{-3}$% while the concentration of ammonia used was 0.15 M. The difference between FIG. 12(a) and FIG. 12(b) is in the formaldehyde concentration used such that the formaldehyde concentration in FIG. 12(a) was 0.7 M and the formaldehyde concentration in FIG. 12(b) was 0.43 M.

Comparative Example 1

The gold nano-shells made according to Example 1 are compared with the gold nano-shells made according to a conventional method which does not use the micro-fluidic device of the present invention. This conventional method is adapted from Graf and Blaaderen (Langmuir 2002, 18, 524-534) and is as follows.

Silica spheres with a low polydispersity were obtained by first preparing small silica seed particles having a radius of 35 nm 35.41 g of tetraethoxysilane (TES, ≥98.0%, obtained from Fluka of Sigma-Aldrich of Missouri of the United States of America) and 43 mL of ammonia (29.3 wt % $NH_3$ obtained from Merck & Co., Inc. of New Jersey of the United States of America) were added to 1000 mL of ethanol (obtained from Merck & Co., Inc. of New Jersey of the United States of America) to obtain final concentrations of 0.17 M TES, 0.69 M $NH_3$ and 1.56 M $H_2O$. In the subsequent reaction steps, these particles were grown larger by seeded growth. In every step, the dispersions were diluted to silica volume fractions of 0.5% and the ammonia and water concentrations were kept at 0.69 M $NH_3$ and 1.56 M $H_2O$. TES (30 mL, 0.134M) was added per 1000 mL of dispersion for each step. Seven and eleven seeded growth steps, respectively, were needed to reach final particle radii of 99 and 205 nm. These silica particles were functionalized with 3-amino-propyltrimethoxysilane (APS, ≥97%, obtained from Fluka of Sigma-Aldrich of Missouri of the United States of America). The amount of APS was calculated to be sufficient to provide an approximate 2.5 monolayer coating on the silica particles. The area on the nano-particle surface covered by each organosilane molecule was assumed to be nominally 0.6 nm.

Aqueous solutions of small gold nanoclusters (1 to 2 nm in diameter) were prepared by reduction of chloroauric acid with tetrakishydroxymethylphosphonium chloride (80% aqueous solution, obtained from Sigma-Aldrich of Missouri of the United States of America). The concentrations of these gold nanocluster solutions were calculated assuming that all chloroauric acid was reduced to 1.5 nm diameter gold clusters. A freshly prepared gold nanocluster solution (50 mL, $c\approx9.9\times10^{-6}$ mol/L) was diluted with 150 mL of water. Then the amount of silica colloids required to provide a surface area of silica equal to 2.5 times the total cross-sectional area of the small gold nanoclusters was estimated. The corresponding volume of silica spheres solution (for example, 185 mg of APS-functionalized silica spheres of 205 nm radius in 21.7 mL of ethanol) was diluted with ethanol to 50 mL and added dropwise to the aqueous gold nanocluster solution within 5 minutes under magnetic stirring (600 rpm). Next, the solution was stirred for another 12 hours.

To remove unattached small gold nanoclusters, the solution was centrifuged (200 g), the supernatant was removed and the remaining light brown pellet was redispersed in water. To prevent the growth of pure gold particles during the formation of the gold shell, this centrifugation/redispersion step was repeated until the supernatant practically contained no small gold nanoclusters anymore. Finally, the precursor particles were redispersed in 100 mL of water and allowed to age in a refrigerator for about 1 week.

In order for the shell to grow, an aliquot (17.4 mL) of a 25 mM chloroauric acid stock solution was diluted with 982.6 mL of water; then 249 mg (1.8 mM) of potassium carbonate was added and the resulting solution was aged at least 1 day in the dark. To initiate growth of the gold shell, the precursor silica particles covered with the small gold clusters were added to the aged $HAuCl_4/K_2CO_3$ solution. The ratio of the amount of the precursor particles added to the volume of the gold salt solution depended on the intended thickness of the gold shells. To this mixture, stirred with a magnetic bar (600 rpm), a freshly prepared hydroxylamine hydrochloride solution (130 mg/L; 1.87 mM) was added dropwise with a dropping funnel in 45 minutes. To concentrate the colloidal gold shells for further characterization and to remove excess reagents, these suspensions were centrifuged (50 g). FIG. 13 shows the particle size distribution of the population of gold nano-shells synthesized using the above method. The histogram of the nano-shells produced by this method exhibits a bimodal distribution and show a large particle size distribution. Some possible configurations of the coated particles are also schematically represented in FIG. 13. Hence, it is possible that more than one core particle may be encapsulated by the gold nano-shell. Further, the particle shape cannot be controlled adequately, resulting in some particles which have an oval shape.

In comparison to the particles generated according to Example 1, it can be seen that the particles of Example 1 have a unimodal particle size distribution and have one silica core per nano-particle. Further, the method of Example 1 can allow for precise control of the shape and size of the nano-particles by controlling the reagent concentrations and volume fraction of gold-seeded silica particles ($f_S$) as can be seen from FIG. 7(a) to FIG. 7(c) where the thickness of the nano-shell can be tuned accordingly. Further, the method of Example 1 is a simpler method than the method described in this comparative example 1 since the method of Example 1 involves fewer steps and requires a shorter period of time. The particles produced from Example 1 are uniformly sized unaggregated particles requiring no postsynthesis treatment. There is also no a priori limitation on the silica core sizes that can be used: this method can handle the full range of typical core sizes used for plasmonic nanoshell fabrication (50 to 500 nm).

Comparative Example 2

In this Comparative Example 2, a micro-fluidic device based on two-phase immiscible fluids was used to form gold nano-shells based on the same reagents and seed particles as demonstrated above in Example 1. Referring to FIG. 14, there is provided a schematic diagram of the two-phase immiscible fluids where similarly to Example 1, oil is introduced into the micro-channel as the continuous phase while reagents such as an aqueous mixture of gold-seeded silica particles and gold plating solution (similarly denoted by "S") and an aqueous reducing agent solution (similarly denoted by "R") were introduced into the micro-channel at the T-junction. The same "S" and "R" solutions as those in Example 1 were used in this Comparative Example 2. The flow rate of the oil stream was 30 μL/min; the flow rate of the "S" stream was 15 μL/min; and the flow rate of each "R" stream was 5 μL/min.

As shown in FIG. 14, the aqueous cells form in the non-polar liquid and the gold nano-shells are envisioned to grow inside each aqueous cell. A time duration of 30 minutes is required in order to collect sufficient quantity of the sample which has a volume of about 0.6 to 1 ml. However, when the actual experiment was carried out, it was found that the micro-fluidic device completely blocked within 10 to 15 minutes of the experiment such that no sample can be collected. FIG. 15 is a photographic image of the micro-fluidic device fouling after 10 to 15 minutes. Hence, the two-phase approach to forming gold nano-shells cannot be used because the micro-fluidic device suffers from fouling problem and no samples can actually be collected from such a micro-fluidic device. Accordingly, the gas phase is required in order to buffer between the individual aqueous cells and ensure that the aqueous cells remain compartmentalized.

Applications

Synthesis of metallic nanoparticles and nanoshells are used as examples in this invention to demonstrate that the ordered microfluidic composite foams can enable robust, automated, scalable and continuous colloidal syntheses of nanostructures. The sensitive dependence of optical properties on particle morphology, composition of these particles implies that the synthesis of particle populations with tightly controlled and narrow particle size distributions is a pre-requisite for their use in practical applications.

The ordered microfluidic composite foams possess a unique set of structural and functional features that make them attractive for processing of specialty nano-particles of high economic interest with their tunable properties based on their composition shape and size. In other words, it is a continuous train of isolated micro-liter droplets containing syntheses mixture in which each droplet goes through an exact and controlled physical and chemical treatment for their growth. The ordered microfluidic composite foams thus generated can enable gas-liquid based colloidal and sol-gel syntheses of sub-micron structures unachievable by current macro- and microscale synthesis methods.

The disclosed micro-fluidic device may not be fouled easily. Due to the presence of the composite foams within the disclosed micro-fluidic device that are effectively shielded from the walls of the micro-channel by the continuous non-polar liquid phase, aggregation and deposition of nano-particles on the micro-channel walls are effectively minimized or negated altogether such that the product quality can be ensured and maintained over time. Further, the micro-channel may not need to undergo additional cleaning steps to remove any nano-particle deposited on the micro-channel walls as would be required in a conventional method which does not employ the composite foams of the present invention.

The nano-particles made from the examples disclosed herein may be used as important components in several nascent but promising applications ranging from nanomedicine, sensors, and chemical catalysis to nanoscale optical circuits and plasmonic invisibility cloaks.

The disclosed micro-fluidic device has potential in industrial scale size controlled continuous production of, pharmaceutical formulations for drug encapsulation and stabilization, nanoparticles for dye sensitized and quantum dots based solar cells, additives and electrodes for fuel cells, biomedical diagnostics, imaging and treatment via surface enhanced raman spectroscopy (SERS) or surface plasmon spectroscopy (SPR) and laser ablation for thermolysis and laser assisted drug delivery, sub-micron particles for electrolytes and electrodes in photo detectors and batteries, and a myriad of other nanoparticle applications.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A method for synthesizing colloidal nanoparticles via making a reactive three-phase foam, wherein the method comprises:
   injecting at least two fluids into a microchamber, wherein one or more of said at least two fluids is immiscible with one or more of the other of said at least two fluids;
   mixing said at least two fluids that are immiscible with each other to form a two-phase fluid flow wherein one phase of said two-phase fluid comprises seeded nanoparticles and reactants;
   pinching off said at least two fluids at a junction in said microchamber, said junction being in fluid communication with a continuous phase conduit, to alternate the at least two phases flowing into said conduit; and
   coating said two-phase fluid flow with a continuous phase to form a three-phase foam for synthesizing said colloidal nanoparticles from said reactants and said seeded nanoparticles.

2. The method of claim 1, wherein the mixing comprises mixing said at least two fluids in a microchamber.

3. The method of claim 2, further comprising injecting said at least two fluids at substantially equal pressures into the microchamber.

4. The method of claim 3, wherein the injecting step comprises injecting said at least two fluids at pressures that vary by no more than 10% from each other.

5. The method of claim 3, wherein said at least two fluids are injected into said microchamber via respective inlet conduits.

6. The method of claim 5, wherein the inlet conduits are connected to said microchamber at about 30 degrees to about 150 degrees relative to a junction.

7. The method of claim 1, wherein said at least two fluids that are immiscible with each other comprise at least an aqueous fluid and a gas fluid.

8. The method of claim 2, wherein said at least two fluids are mixed in the laminar region, wherein laminar flow, Re, is less than 1000 but greater than 0.1.

9. The method of claim 1, wherein said continuous phase comprises an oil fluid.

10. The method of claim 7, wherein said aqueous fluid phase and said gas fluid phase are immersed in the continuous phase comprising an oil fluid.

11. The method of claim 10, wherein the ratio of the flow rate of the oil fluid to the flow rate of the aqueous fluid phase is from about 0.1 to about 2.0.

12. The method of claim 1, wherein said three-phase foam further comprises an alternating aqueous fluid phase and gas fluid phase immersed in the continuous phase.

13. The method of claim 10, wherein said gas fluid phase comprises an inert gas.

14. The method of claim 10, wherein said gas fluid phase comprises the reactants to produce said colloidal nanoparticles.

15. The method of claim 14, wherein said aqueous fluid phase is reactive to produce the colloidal nanoparticles.

16. The method of claim 1, wherein said synthesized colloidal nanoparticles have a substantially uniform particle size distribution with ±5% deviation from the average particle diameter.

17. The method of claim 7, wherein the aqueous fluid and gas fluid are in alternating phases and are immersed in the continuous phase.

* * * * *